US009402596B1

(12) United States Patent
Sheu et al.

(10) Patent No.: US 9,402,596 B1
(45) Date of Patent: Aug. 2, 2016

(54) BOWEL SOUND ANALYSIS METHOD AND SYSTEM

(71) Applicant: CHIMEI MEDICAL CENTER, Tainan (TW)

(72) Inventors: Ming-Jen Sheu, Tainan (TW); Jen-Yin Chen, Tainan (TW); Jhi-Joung Wang, Tainan (TW); Bor-Shyh Lin, Tainan (TW)

(73) Assignee: Chimei Medical Center, Tainan (TW)

( * ) Notice: Subject to any disclaimer, the term of this patent is extended or adjusted under 35 U.S.C. 154(b) by 51 days.

(21) Appl. No.: 14/593,126

(22) Filed: Jan. 9, 2015

(51) Int. Cl.
*A61B 5/00* (2006.01)
*A61B 7/00* (2006.01)
*A61B 5/11* (2006.01)
*A61B 7/04* (2006.01)

(52) U.S. Cl.
CPC .............. *A61B 7/008* (2013.01); *A61B 5/0004* (2013.01); *A61B 5/0017* (2013.01); *A61B 5/1107* (2013.01); *A61B 5/4255* (2013.01); *A61B 5/7203* (2013.01); *A61B 5/7239* (2013.01); *A61B 5/7278* (2013.01); *A61B 5/742* (2013.01); *A61B 7/04* (2013.01)

(58) Field of Classification Search
CPC ...... A61B 5/42; A61B 5/4222; A61B 5/4255; A61B 7/02; A61B 7/023; A61B 7/026; A61B 7/008
See application file for complete search history.

(56) References Cited

U.S. PATENT DOCUMENTS

| | | | | |
|---|---|---|---|---|
| 6,228,040 B1 * | 5/2001 | Craine | ................... | A61B 7/008 600/586 |
| 6,776,766 B2 * | 8/2004 | Sandler | ................. | A61B 7/008 600/587 |
| 6,840,913 B2 * | 1/2005 | Mansy | ................... | A61B 7/008 600/586 |
| 8,475,396 B2 * | 7/2013 | Jones | ..................... | A61B 7/026 600/586 |
| 9,179,887 B2 * | 11/2015 | Cromwell | ............. | A61B 7/008 |

* cited by examiner

*Primary Examiner* — Max Hindenburg
(74) *Attorney, Agent, or Firm* — Rosenberg, Klein & Lee

(57) ABSTRACT

A bowel sound analysis method and system utilizes an audio collection apparatus to continuously monitor an abdominal cavity of an examinee and collect a bowel sound signal of an intestinal tract inside the abdominal cavity, converts the bowel sound signal into a digital signal, then removes noise from the digital signal by using higher-order statistics (HOS) and captures a high-complexity feature from the digital signal by using fractal dimension algorithm, and subsequently defines the high-complexity feature as an intestinal motility signal. Therefore, according to the intestinal motility signal, a time point when intestinal motility occurs in the intestinal tract inside the abdominal cavity of the examinee can be learned, and bowel sound features such as the amplitude, frequency, and period of the intestinal motility signal may further be analyzed to determine a health condition of the intestinal tract.

8 Claims, 6 Drawing Sheets

BOWEL SOUND ANALYSIS METHOD AND SYSTEM

BACKGROUND

1. Technical Field

The present invention relates to a bowel sound analysis method and system, and more particularly to a bowel sound analysis method and system that removes, by using higher-order statistics (HOS), noise from a continuously collected bowel sound signal, then captures a high-complexity feature by using a fractal dimension algorithm to obtain an intestinal motility signal to determine a time point when intestinal motility occurs, and may further analyze a feature of the intestinal motility signal to determine a health condition of an intestinal tract.

2. Related Art

According to the statistics data of Ministry of Health and Welfare of ROC in 2012, malignant neoplasm (cancer) was still listed first among the top ten leading causes of death. On average, one person died of cancer every twelve minutes and two seconds, and colorectal cancer still ranked third among the top ten cancers. Motility diseases caused by gastrointestinal problems are common internal and surgical diseases. One of the most common gastrointestinal motility disorders, Ileus, can occur following cancer surgery and laparoscopic surgery, appear with infections, abdominal inflammation, endocrine diseases, or present as drug side effects.

The use of gastroscopy and computed tomography may assist a physician to observe organs directly; however, the practicability of gastroscopy and computed tomography are actually limited by some constraints. For example, computed tomography instruments are very expensive, gastroscopy requires direct entry into intestines and easily causes discomfort during examination, and both computed tomography and gastroscopy require professional training of operations and high demands for medical labor. Computed tomography and gastroscopy are also unsuitable for long-term monitoring and measurement on a patient.

Therefore, a clinically common diagnosis manner is to observe a condition of intestinal motility by using a nonintrusive stethoscope, and a health condition of a gastrointestinal tract of a patient is diagnosed based on the amplitude, frequency, and period of bowel sound. However, the use of a conventional stethoscope to observe a condition of intestinal motility must rely on a physician with rich clinical experience, and the quality of stethoscopy is affected by training and experience of an examiner, environment, and abdominal condition changes, and objective evaluation such as quantization of intestinal motility conditions of a patient cannot be easily performed. Therefore, it becomes a topic of concern at present how to achieve the most effective and accurate application for evaluation and diagnosis of bowel sound.

SUMMARY

To quantize bowel sound for doctors or nurses to accurately determine a health condition of an intestinal tract of a patient, the present invention provides a bowel sound analysis method, which includes the following steps:

A. continuously monitoring an abdominal cavity of an examinee within a specific time by using an audio collection apparatus, and collecting a bowel sound signal of an intestinal tract inside the abdominal cavity; B. converting the bowel sound signal into a digital signal; C. a processing unit removing noise from the digital signal by using HOS; D. the processing unit then capturing a high-complexity feature from the digital signal by using a fractal dimension algorithm, and defining the high-complexity feature as an intestinal motility signal; and E. learning, according to the intestinal motility signal, a time point when intestinal motility occurs in the intestinal tract inside the abdominal cavity.

Further, in Step D, the processing unit analyzes, according to the intestinal motility signal, at least one of the following feature values: the number of times that the intestinal motility signal appears within a unit time, the duration of the intestinal motility signal, the maximum signal intensity of the intestinal motility signal, the maximum root-mean-square intensity of the intestinal motility signal, the major distribution frequency of the intestinal motility signal, and the power of the intestinal motility signal.

Further, each of the aforesaid signals is transmitted to a remote computer to perform remote monitoring.

The present invention further provides a bowel sound analysis system using the bowel sound analysis method, including:

an audio collection apparatus, used to continuously collect a bowel sound signal within a specific time; a bowel sound capturing and analysis module, connected to the audio collection apparatus, wherein the bowel sound capturing and analysis module includes an audio sensing circuit, a preamplification circuit, and a processing unit; and an output interface, connected to the bowel sound capturing and analysis module.

The audio sensing circuit receives the bowel sound signal, and converts the bowel sound signal into an electric signal. The preamplification circuit amplifies and filters the electric signal. The processing unit converts the electric signal into a digital signal, removes noise from the digital signal by using HOS, captures a high-complexity feature from the digital signal by using a fractal dimension algorithm, and defines the high-complexity feature as an intestinal motility signal. The output interface is used to output the various signals.

Further, an environmental noise elimination apparatus is disposed on the audio collection apparatus and used to eliminate environmental noise.

Further, the output interface is a display; or the output interface is a wireless transmission module, and a signal of a remote computer is connected to the wireless transmission module. The wireless transmission module is any one of an infrared transmission module, radio, Bluetooth, ZigBee, 2G, 2.5G, 2.75G, 3G, Wi-Fi, and WiMAX.

The efficacy of the present invention lies in that:

1. Through long-term and automatic detection of a bowel sound signal, high noise immunity where noise is removed by using HOS, and the use of fractal dimension signal processing technology to help a physician to automatically determine a time point when an intestinal motility event occurs, intestinal motility status may be monitored for a long term for patients having abdominal symptoms such as irritable bowel syndrome, abdominal distention, abdominal pain, constipation, and diarrhea. In addition, precise evaluation is made for abdominal diagnosis, and a physician is thus enabled to track and detect in time abnormal changes of intestinal tract motility and influences on the intestinal tract caused by drugs or treatment.

2. In terms of measurement, abdominal bowel sound of a patient is captured in a nonintrusive manner, and therefore inconvenience and discomfort caused to a patient are avoided. Compared with conventional, expensive medical instruments, the present invention can reduce many medical costs and also utilize manual labor effectively. In mechanical design, small sizes and portability may be adopted to improve the convenience in system use.

3. A wireless transmission technology may be used at the same time. Various detected signals and feature values of an intestinal motility signal are transmitted in real time to a rear-end computer for analysis, so as to improve convenience in operations for a physician.

BRIEF DESCRIPTION OF THE DRAWINGS

The present disclosure will become more fully understood from the detailed description given herein below for illustration only, and thus are not limitative of the present disclosure, and wherein.

DETAILED DESCRIPTION

In combination with the foregoing technical features, the major efficacy of a bowel sound analysis method and system of the present invention is clearly presented in the following embodiments.

Figure 1:
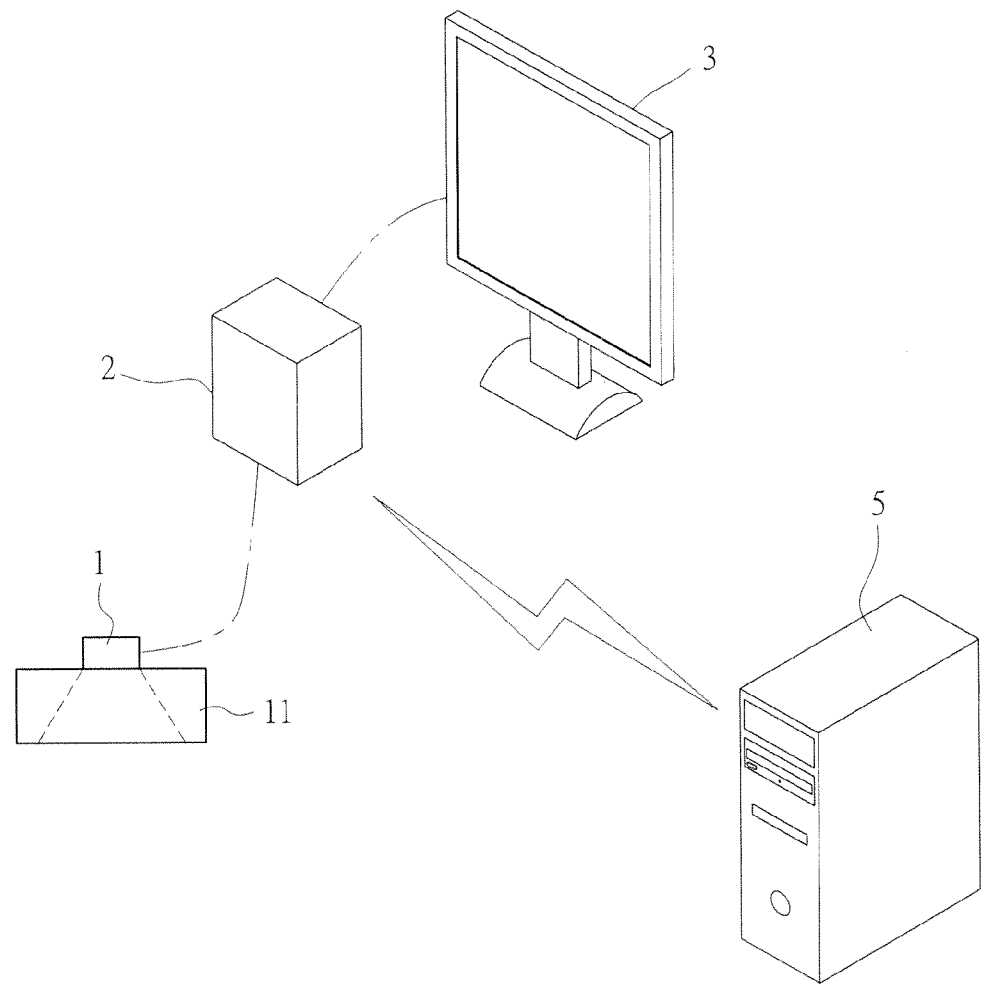
FIG. 1 is an architecture view of a bowel sound analysis system according to an embodiment of the present invention.
Figure 2:
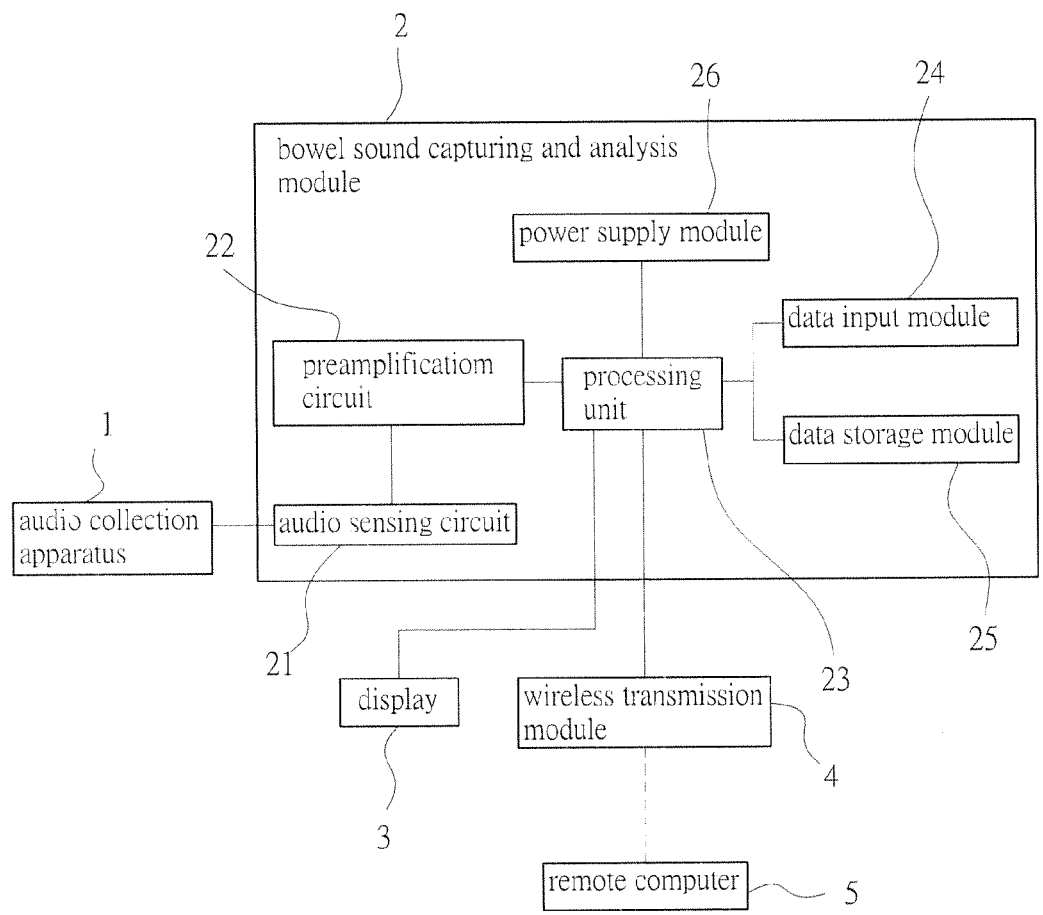
FIG. 2 is a functional block diagram of each means in a bowel sound analysis system according to an embodiment of the present invention.

Referring to FIG. 1 and FIG. 2, a bowel sound analysis system in this embodiment includes an audio collection apparatus (1), a bowel sound capturing and analysis module (2), and an output interface.

The audio collection apparatus (1) is, for example, a stethoscope, and an environmental noise elimination apparatus (11) is disposed on the audio collection apparatus (1). The environmental noise elimination apparatus (11) may be a cylindrical sound-proof apparatus, and a material, for example, acoustic absorption foam, that can absorb external environmental noise may be used in the environmental noise elimination apparatus (11). The bowel sound capturing and analysis module (2) is connected to the audio collection apparatus (1). The bowel sound capturing and analysis module (2) includes an audio sensing circuit (21), a preamplification circuit (22), a processing unit (23), a data input module (24), a data storage module (25), and a power supply module (26). The output interface is connected to the bowel sound capturing and analysis module (2). In this embodiment, the output interface includes a display (3) and a wireless transmission module (4), and a signal of a remote computer (5) is connected to the wireless transmission module (4). The wireless transmission module (4) may be any one of an infrared transmission module, radio, Bluetooth, ZigBee, 2G, 2.5G, 2.75G, 3G, Wi-Fi, and WiMAX.

Figure 3:
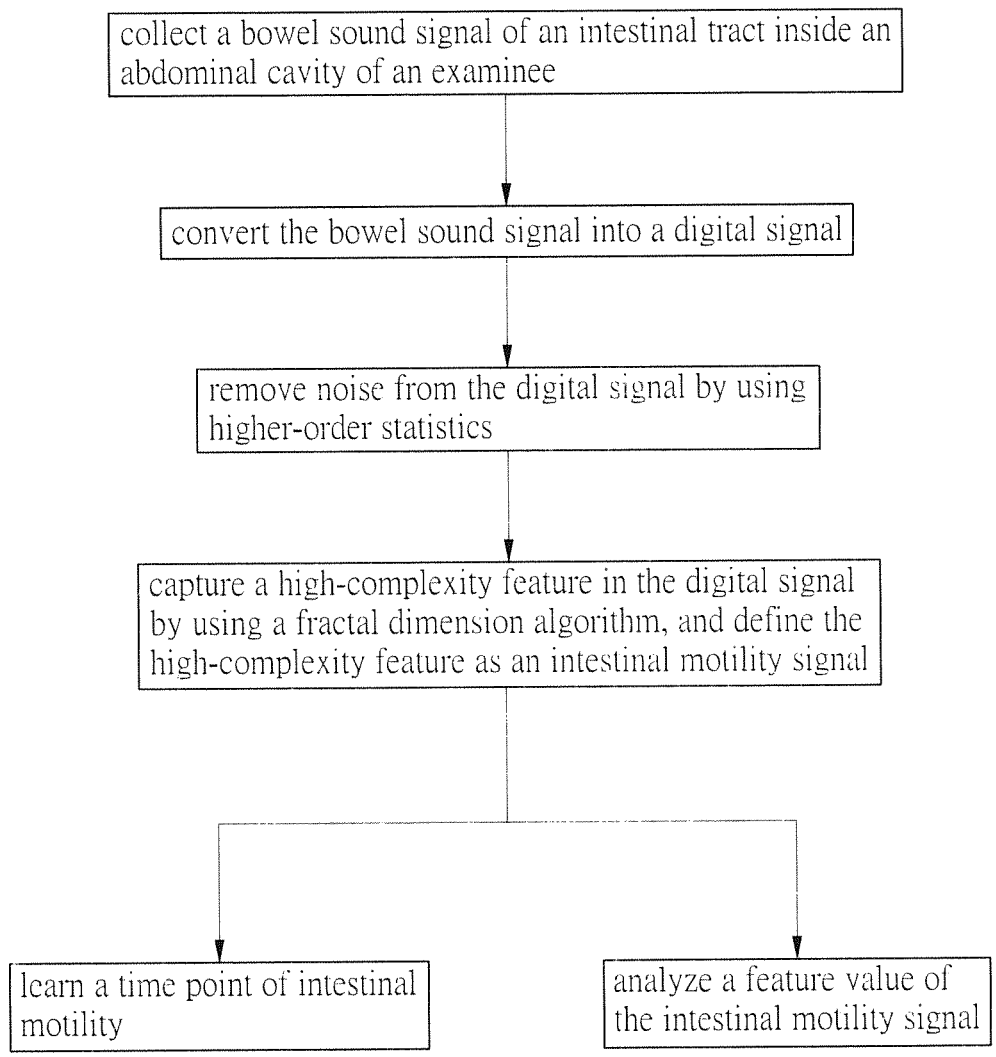
FIG. 3 is a flow chart of a bowel sound analysis method according to an embodiment of the present invention.

Further referring to FIG. 3, a bowel sound analysis method in this embodiment is executed by the foregoing bowel sound analysis system, and includes the following steps:

A. The audio collection apparatus (1) continuously monitors an abdominal cavity of an examinee within a specific time, and collects a bowel sound signal of an intestinal tract inside the abdominal cavity. The specific time is set by a doctor or nurse according to different conditions of the examinee. For example, the examinee has received an abdominal surgery, and it usually takes 3 to 5 days for large intestines to restore normal functions after an abdominal surgery; therefore, the specific time may be set to be 3 to 5 days or a longer time. The environmental noise elimination apparatus (11) may preliminarily filter environmental noise, and therefore the method may be used in common hospital environments.

Figure 4:
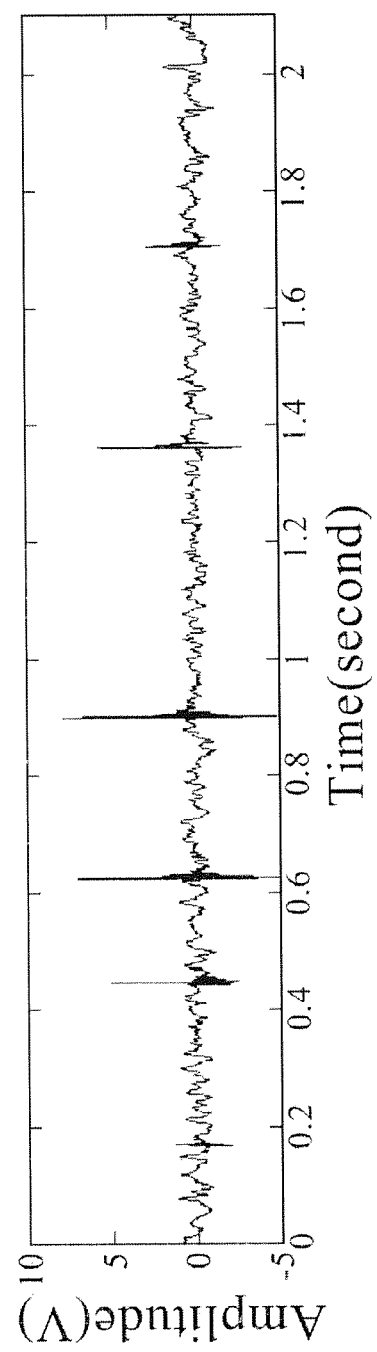
FIG. 4 is an oscillogram of converting a bowel sound signal into a digital signal in a bowel sound analysis method according to embodiment of the present invention.

B. With reference to FIG. 4, the audio sensing circuit (21) is used to receive the bowel sound signal, and convert the bowel sound signal into an electric signal, the preamplification circuit (22) then performs amplification and filtering processing on the electric signal, and subsequently the processing unit (23) converts the electric signal into a digital signal.

Figure 5:
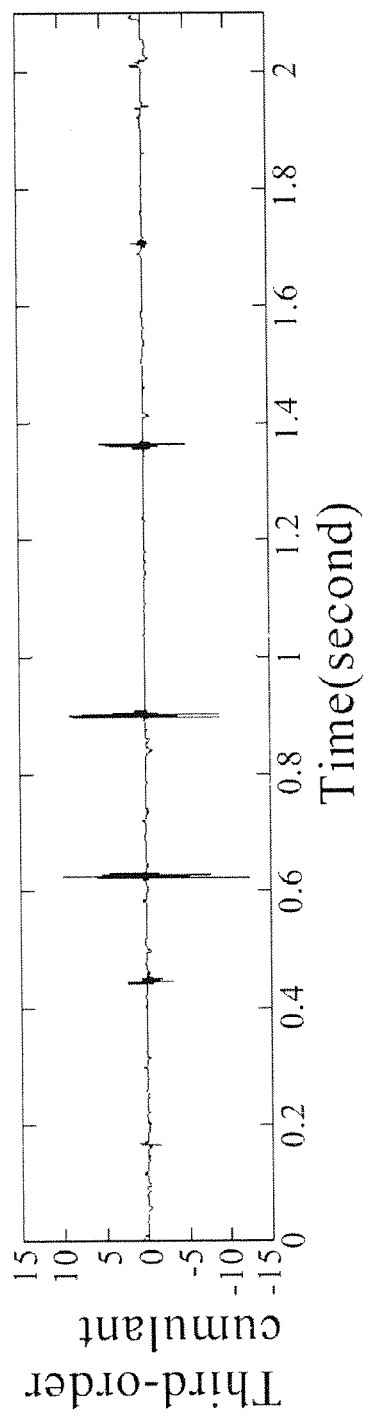
FIG. 5 is an oscillogram of a digital signal from which noise is removed by using HOS in a bowel sound analysis method according to an embodiment of the present invention.

C. With reference to FIG. 5, the bowel sound signal has non-Gaussian features and unsteady characteristics, and a higher-order statistical technology has a characteristic of inhibiting Gaussian noise and keeping non-Gaussian signals; therefore, in the present embodiment, the processing unit (23) removes noise from the digital signal by using higher-order statistics (HOS), and HOS in this embodiment performs calculation to the third-order statistics:

(1) $z(t)=s(t)+n_s(t)$ where $Z(t)$ is a raw bowel sound signal, $S(t)$ is a clear bowel sound signal, and $n_s(t)$ is added noise.

$$C_{zzz}(t;\tau_1,\tau_2)=\lambda C_{zzz}(t-1;\tau_1,\tau_2)+(1-\lambda)z(t)z(t+\tau_1)z(t+\tau_2)$$

where $C_{ZZZ}$ is a third-order cumulant of the raw bowel sound signal $Z(t)$, $\tau_1$, $\tau_2$ are time difference quantities of the raw bowel sound signal $Z(t)$, and $\lambda$ is a forgetting factor.

$$\tau_1=-m_1,(-m_1+1),\ldots,(m_1-1),m_1, \tau_2=1,2\ldots,m_2,$$
where $m$ is a positive integer.

$\hat{C}_{zzz}(t)=\text{mean}[C_{zzz}(t;\tau_1,\tau_2)]$ is a mean operator.

(2) Initial conditions:

$$C_{zzz}(0,\tau_1,\tau_2)=0, \tau_1=-m_1,(-m_1+1),\ldots,(m_1-1),m_1, \tau_2=1,2\ldots,m_2$$

$$n_{C_{zzz}}=W$$

$n_{C_{zzz}}$ is the number of steps for $C_{zzz}$ in moving window, and $W$ is moving window length for fractal dimension analysis.

(3) Let $Z(t)$ be a zero-mean signal:

$$z(t)=z(t)-\text{mean}[z(t)]$$

A higher-order statistical value of the digital signal may be obtained by using the foregoing algorithm. $C_{ZZZ}(t;\tau_1,\tau_2))$ includes $C_{SSS}(t;\tau_1,\tau_2)$ and $C_{n_s n_s n_s}(t;\tau_1,\tau_2)$, $C_{SSS}(t;\tau_1,\tau_2)$ is a third-order cumulant of the clear bowel sound signal, and $C_{n_s n_s n_s}(t;\tau_1,\tau_2)$ is a third-order cumulant of the added noise. Assuming that the added noise $n_s$ is Gaussian noise and the order of the higher-order cumulant is greater than 2 (n>2), the higher-order cumulant of the added noise will be inhibited and in this way, noise is filtered out.

Figure 6:
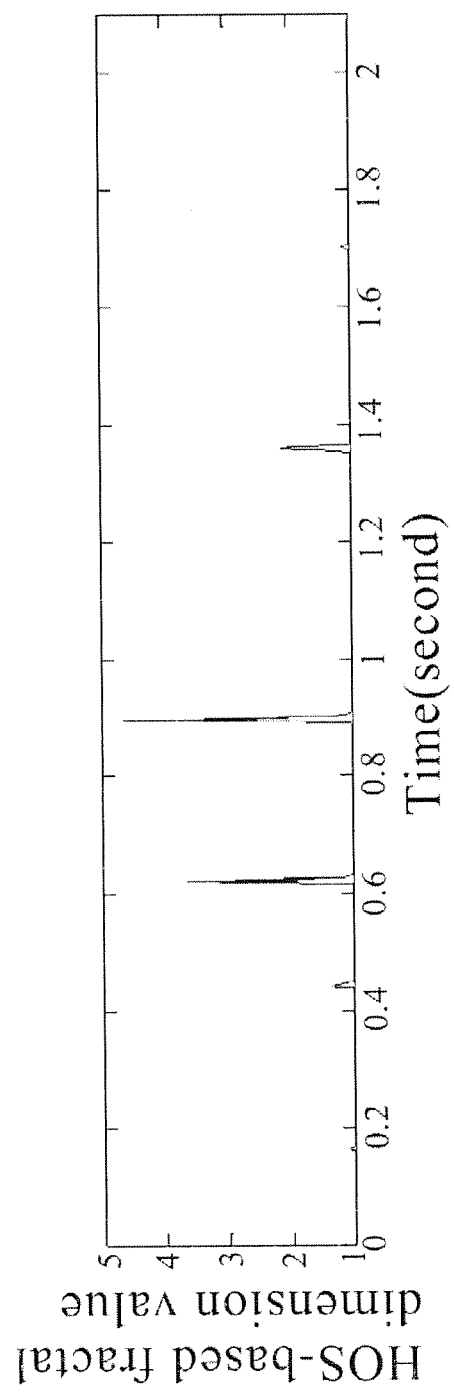
FIG. 6 is an oscillogram of an intestinal motility signal obtained by using a fractal dimension algorithm in a bowel sound analysis method according to an embodiment of the present invention.

D. With reference to FIG. 6, the processing unit (23) then captures a high-complexity feature from the digital signal by using an HOS-based fractal dimension algorithm, and defines the high-complexity feature as an intestinal motility signal.

(1) Calculate total length of $C_{zzz}$ in moving window:

$$L_{C_{zzz}}(t) = \sum_{k=t}^{t+W-1} dist\left[\hat{C}_{zzz}(k-W), \hat{C}_{zzz}(k-W+1)\right]$$

where dist[.] denotes a distance between two adjacent points in moving window.

(2) Calculate a diameter of $C_{zzz}$ in moving window:

$$d_{C_{zzz}}(t) = \max[dist[\hat{C}_{zzz}(t-W), \hat{C}_{zzz}(k)]], k=t-W+1, t-W+2, \ldots, t$$

(3) Estimation of HOS-based fractal dimension:

$$FD_{C_{zzz}}(t) = \frac{\log_{10}(n_{C_{zzz}})}{\log_{10}(n_{C_{zzz}}) + \log_{10}\left(\frac{d_{C_{zzz}}(t)}{L_{C_{zzz}}(t)}\right)}$$

E. In the digital signal that is processed by using the foregoing HOS-based fractal dimension algorithm, a time point when intestinal motility occurs may be marked, and further, in the step, the processing unit (23) may analyze, according to the intestinal motility signal, at least one of the following feature values: the number of times that the intestinal motility signal appears within a unit time, the duration of the intestinal motility signal, the maximum signal intensity of the intestinal motility signal, the maximum root-mean-square intensity of the intestinal motility signal, the major distribution frequency of the intestinal motility signal, and the power of the intestinal motility signal, and the like. Doctors or nurses can perform objective analysis and determination on a health condition of an intestinal tract of an examinee according to the foregoing quantized feature values.

It should be further noted that the data input module (24) may be a button, a keyboard, a touch panel or a combination of the foregoing, and is used to operate the menu of such a system and set system parameters. The data storage module (25) is a storage-related apparatus such as a RAM, a ROM, a FLASH DISK or hard disk and is used to store system-related parameters, measured signal values, and the like. The power supply unit (26) is used to supply power to the system. The various signals and analyzed feature values in the foregoing may be directly displayed by the display (3); or the various signals and analyzed feature values may also be transmitted to the remote computer (5) by using the wireless transmission module (4), for example, transmitted from a ward to a computer in a nursery or a surgery, thanks to the convenience in use.

The operations and use of the present invention and the efficacy produced by the present invention may be fully understood with reference to the description of the foregoing embodiments, and the above embodiments are merely preferred embodiments of the present invention and are not intended to limit the scope of the implementation of the present invention. Simple, equivalent changes and modifications made to the claims and the specification of the present invention all fall within the scope of the present invention.

What is claimed is:

1. A bowel sound analysis method, comprising the following steps:
    A. continuously monitoring an abdominal cavity of an examinee within a specific time by using an audio collection apparatus, and collecting a bowel sound signal of an intestinal tract inside the abdominal cavity;
    B. converting the bowel sound signal into a digital signal;
    C. using higher-order statistics (HOS), by a processing unit, to remove noise from the digital signal;
    D. using a fractal dimension algorithm, by the processing unit, to capture a high-complexity feature from the digital signal, and defining the high-complexity feature as an intestinal motility signal; and
    E. learning, according to the intestinal motility signal, a time point when intestinal motility occurs in the intestinal tract inside the abdominal cavity.

2. The bowel sound analysis method according to claim 1, in Step D, the processing unit further analyzes, according to the intestinal motility signal, at least one of the following feature values: the number of times that the intestinal motility signal appears within a unit time, the duration of the intestinal motility signal, the maximum signal intensity of the intestinal motility signal, the maximum root-mean-square intensity of the intestinal motility signal, the major distribution frequency of the intestinal motility signal, and the power of the intestinal motility signal.

3. The bowel sound analysis method according to claim 1, each signal is further transmitted to a remote computer to perform remote monitoring.

4. A bowel sound analysis system, comprising:
    an audio collection apparatus, used to continuously collect a bowel sound signal within a specific time;
    a bowel sound capturing and analysis module, connected to the audio collection apparatus, wherein the bowel sound capturing and analysis module includes an audio sensing circuit, a preamplification circuit, and a processing unit; and
    an output interface, connected to the bowel sound capturing and analysis module; wherein
    the audio sensing circuit receives the bowel sound signal, and converts the bowel sound signal into an electric signal; the preamplification circuit amplifies and filters the electric signal; the processing unit converts the electric signal into a digital signal, removes noise from the digital signal by using higher-order statistics (HOS), captures a high-complexity feature from the digital signal by using a fractal dimension algorithm, and defines the high-complexity feature as an intestinal motility signal; and the output interface is used to output the various signals.

5. The bowel sound analysis system according to claim 4, wherein an environmental noise elimination apparatus is disposed on the audio collection apparatus.

6. The bowel sound analysis system according to claim 4, wherein the output interface is a display.

7. The bowel sound analysis system according to claim 4, wherein the output interface is a wireless transmission module, and a signal of a remote computer is connected to the wireless transmission module.

8. The bowel sound analysis system according to claim 7, wherein the wireless transmission module is any one of an infrared transmission module, radio, Bluetooth, ZigBee, 2G, 2.5G, 2.75G, 3G, Wi-Fi, and WiMAX.

* * * * *